United States Patent [19]

Kindlund et al.

[11] 4,399,686
[45] Aug. 23, 1983

[54] GAS DETECTOR

[75] Inventors: Alf R. Kindlund; Kurt I. Lundström, both of Linköping, Sweden

[73] Assignee: Engström Medical AB, Bromma, Sweden

[21] Appl. No.: 231,942

[22] Filed: Feb. 5, 1981

[30] Foreign Application Priority Data

Feb. 21, 1980 [SE] Sweden ............................. 8001357

[51] Int. Cl.³ .................................. G01N 31/06
[52] U.S. Cl. ................................. 73/23; 422/98
[58] Field of Search .............. 73/23; 422/88, 98; 128/719

[56] References Cited

U.S. PATENT DOCUMENTS

| | | | |
|---|---|---|---|
| 3,164,004 | 1/1965 | King, Jr. | 73/23 |
| 3,260,104 | 7/1966 | King, Jr. | 73/23 |
| 3,266,291 | 8/1966 | King, Jr. | 73/23 |
| 4,150,670 | 4/1979 | Jewett et al. | 73/23 |
| 4,312,228 | 1/1982 | Wohltjen | 73/23 |

OTHER PUBLICATIONS

"Dow Corning 190 Surfactant for Flexible Urethane Foams", Dow Corning Bulletin: 05-128, Jun. 1965.
"Dow Corning 190 Fluid for Flexible Urethane Foams", Dow Corning Bulletin: 05-130, Jun. 1965.
Condensed Chemical Dictionary, Eighth Edition, p. 784, Aug. 1976.

Primary Examiner—Stephen A. Kreitman
Attorney, Agent, or Firm—Browdy & Neimark

[57] ABSTRACT

An apparatus for detecting and measuring the presence and the concentration, respectively, of halogenated hydrocarbons, in particular anaesthetic gases, as halothane, enfluorane, metoxyfluorane and isofluorane, in a mixture of gases comprises a piezoelectric crystal, which has its surface coated with a thin layer of a substrate and which is so arranged that the substrate layer can be brought into contact with the gas mixture. The crystal is coupled to an oscillator circuit which is connected to means for measuring changes in the oscillating frequency of the crystal and thus also of the oscillator circuit caused by adsorption by the substrate layer of the gas component to be detected. The substrate layer comprises a silicone oil having a structural formula comprising large branch chains or pendant blocks. Preferably a silicone oil is used comprising a silicone glycol copolymer.

7 Claims, 5 Drawing Figures

STEELE-2

GAS DETECTOR

The present invention relates to an apparatus for detecting the presence of a given gas component of a mixture of gases.

It is known, e.g. from U.S. Pat. No. 3,164,004, that given gas components of gaseous mixtures can be detected with the aid of a piezoelectric crystal, e.g. a quartz crystal, incorporated in an oscillator circuit. The crystal is coated on one side thereof with a thin substrate layer, and is so arranged that the substrate layer can be brought into contact with the gaseous mixture to be investigated. The substrate layer comprises a substance which is able to reversibly and selectively adsorb the gas component whose presence shall be detected. Molecules of the gas to be detected in the gaseous mixture are adsorbed by the substrate layer, causing the mass of said layer to increase, resulting in a lowering of the vibrational frequency of the piezo electric crystal, and therewith also of the oscillating frequency of the oscillator circuit. It has been found possible when using such an apparatus to detect very small concentrations of a given gas component in a gaseous mixture and also to measure the concentration quantitatively with a high degree of accuracy. One advantageous method of determining the change of frequency of the oscillator circuit as a result of the adsorption and desorption by the substrate layer of the gas component in question is to use an identically similar reference oscillator with a similar piezoelectric crystal which is brought into contact with the same gaseous mixture as the detector crystal but which lacks a substrate layer. By mixing the output frequencies of the two oscillator circuits there is obtained a difference frequency corresponding to the variations in the oscillating frequency of the detector crystal.

As will be described more clearly hereinafter the substrate layer, however, also has other physical properties which are affected by adsorption of the gas component in question in the layer and which can be measured for determining the presence and concentration of the gas components in question in a gaseous mixture.

One primary problem encountered when using the aforedescribed method for detecting the presence of a given gas in a gaseous mixture is to find a substrate material which is suitable for just that particular gas component to be detected. Thus, primarily the substrate material shall be selective with respect to the gas component to be detected, so that substantially only this component is adsorbed, while other components which may be present in the gaseous mixture being investigated, and which in many instances may constitute the substantial part of said mixture, are not adsorbed to any appreciable extent. Further, the substrate material should be highly sensitive to the gas component to be detected, so that the substrate layer is able to adsorb a large number of molecules thereof, even when the concentration of said gas component in the gaseous mixture is low. In this way, large measuring values, which can readily and accurately be determined, are obtained even at low concentrations. The magnitude of the measuring value at a given gas concentration, and therewith the sensitivity of the apparatus, can generally be increased by increasing the thickness of the substrate layer, since the layer is then able to adsorb a larger number of molecules of the gas component to be detected. Finally, in the case of many applications, the substrate material should exhibit a high reaction rate, so that adsorption and desorption of the molecules of the gas component to be detected can take place rapidly. In this way, it is possible to detect and measure rapid variations in the concentration of said gas component in the gaseous mixture. This desideratum, however, has been considered to a certain extent contradictory to the desideratum of high sensitivity, since the thicker substrate layer is considered to adsorb and desorb the molecules of the gas component to be detected more slowly than a thin substrate layer.

An object of the present invention is to provide a gas detecting apparatus of the aforedescribed kind which is able to detect the presence of halogenated hydrocarbons, in particular anaesthetic gases such as halothane, enflourane, methoxyfluorane and isofluorane.

Such a gas detector having exceedingly good properties in all the above mentioned respects is obtained when, in accordance with the invention, the substrate layer comprises a silicone oil whose structural formula contains large branch chains. It has been found of particular advantage to use silicone oils which have large branch chains in the form of polyglycols, such as in particular silicone oils comprising silicone glycol copolymers having the general structural formula

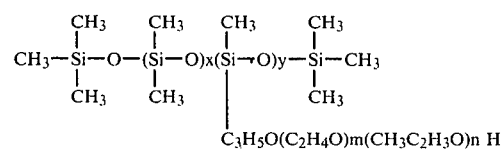

$$C_3H_5O(C_2H_4O)m(CH_3C_2H_3O)n\ H$$

As can be seen, in this type of silicone oils part of the methyl groups in a polydimethylsiloxane are replaced with large polyglycol chains. These silicone oils can, according to CTFA, also be designated dimethicone copolyols. In particular, excellent results have been achieved in detecting the above mentioned anaesthetic gases when using a substrate consisting of silicone oils of the above type produced by Dow Corning Corporation and identified with the product names DC 190 and DC 197, respectively. DC 190 can also be described as a random rake copolymer of a trimethylsilylterminated polydimethylsiloxane with pendant silicone-carbon linked blocks of acetate-capped poly(propylene oxide-ethylene oxide), whereas DC 197 can be described as a random rake copolymer of trimethylsilylterminated polydimethylsiloxane with pendant silicone-carbon linked blocks of hydroxy-terminated poly(ethylene oxide).

It has been mentioned quite generally in the aforementioned U.S. patent specification that silicone oil and certain greases can be used as a substrate material for the non-selective detection of hydrocarbons. It has been discovered, however, through the present invention that silicone oils of the aforementioned particular kind are much superior to silicone oils which lack large branch chains or pendant blocks, with respect to primarily sensitivity but also with respect to selectivity and rate of reaction when wishing to detect halogenated hydrocarbons, and in particular anaesthetic gases of the aforementioned kind.

The invention will now be described in more detail with reference to the accompanying drawing, in which FIG. 1 illustrates schematically and by way of example a conceivable embodiment of a piezoelectric detector for an apparatus according to the invention;

Figure 4:
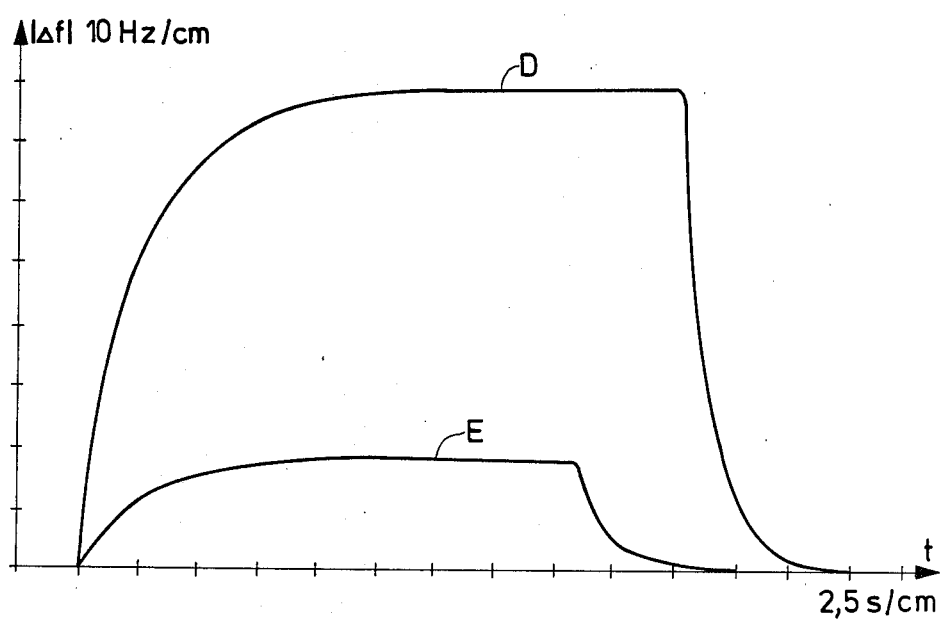

FIG. 4 is a diagram illustrating typical adsorption-desorption processes when detecting halothane with the use of a gas-detecting apparatus provided with a substrate layer comprising a silicone oil according to the invention and a substrate layer comprising a silicone oil which lacks large branch chains or pendant blocks; and FIG. 5 illustrates schematically a horizontal sectional view through an advantageous embodiment of a detector apparatus which includes both a detector crystal and a reference crystal.

Figure 1:
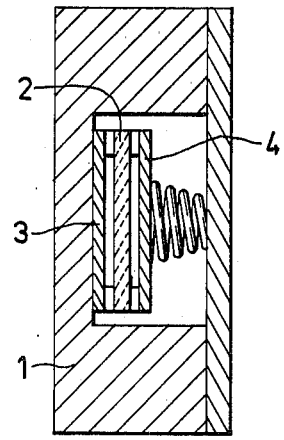

FIG. 1 illustrates schematically, and by way of example, a side view in section of a conceivable embodiment of a piezoelectric detector which can be used with an apparatus according to the invention. The detector comprises a housing 1 which is connected to gas-supply pipes through which the gaseous mixture to be investigated can flow into the detector housing. Arranged within the housing 1 is a piezoelectric crystal 2, for example a quartz crystal, said crystal being mounted between two electrodes 3 and 4 in a manner such that two side surfaces of the crystal 2 are in contact with the gaseous mixture flowing through the detector housing 1. At least one side of the crystal, although preferably both sides of said crystal, is provided with the desired substrate layer. When using a crystal detector of this kind in a gas detector according to the invention, the crystal is incorporated in a suitable oscillator circuit whose oscillating frequency is determined by the vibrational frequency of the piezoelectric crystal 2.

Figure 2:
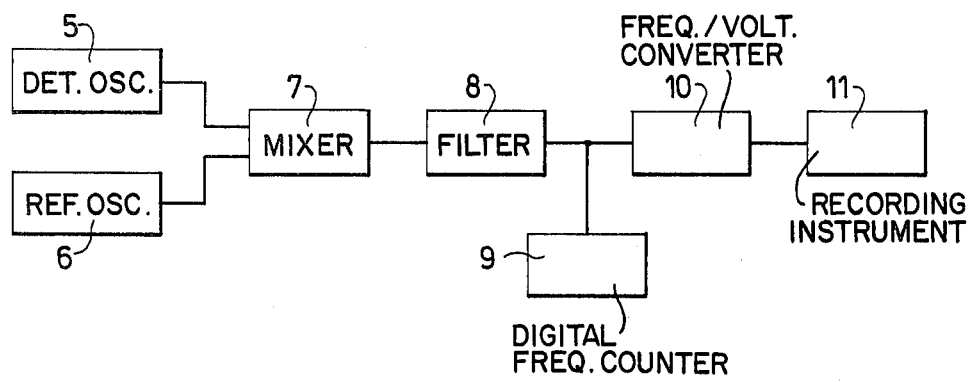
FIG. 2 illustrates schematically a circuit diagram for an exemplary embodiment of an apparatus according to the invention, this apparatus having been used when carrying out the tests described hereinafter.

A detector apparatus having a piezoelectric detector crystal may be constructed in the manner illustrated schematically in FIG. 2. The apparatus includes two oscillators, namely a detector oscillator 5 and a reference oscillator 6. The two oscillators are of exactly the same design and contain identical oscillator crystals, whereas the crystal in the detector oscillator 5, however, is provided with a substrate layer, while the crystal in the reference oscillator 6 lacks such a layer. The output signals from the two oscillators 5 and 6 are applied to a mixer circuit 7, from which there is obtained a signal containing the difference frequency and the summation frequency of the output signals of the two oscillators. The mixer circuit 7 is connected to a filter 8 arranged to allow only the difference frequency to pass through, said difference frequency being displayed by means of a digital frequency counter 9 connected to the filter output. The output signal of the filter 8 is also applied to a frequency-voltage converter 10 whose output voltage can be registered by means of a recording instrment 11, said instrument producing a curve showing the frequency difference between the two oscillators 5 and 6 as a function of time.

In order to obtain an accurate measurement, it is important that the manner in which the gaseous mixture acts on the detector crystal and on the reference crystal is, to the greatest possible extent, precisely the same in both cases. This can be ensured by mounting the two crystals in a common detector housing through which the gaseous mixture is arranged to flow. For example, the arrangement may be that shown schematically in FIG. 5. FIG. 5 is a horizontal sectional view through a detector housing 12 having an inlet 13 and an outlet 14 which are arranged opposite one another and through which a flow of the gaseous mixture to be investigated is intended to pass. Arranged within the housing is a body 15 having two identical and symmetrically located flow passages 16 and 17 for said gas flow, in which passages the detector crystal 18 and the reference crystal 19 are mounted with their side surfaces parallel to the direction of said gas flow and being mutually symmetrical on a respective side of a symmetry plane passing through the total gas flow. In the illustrated embodiment, the crystals are of a kind which are provided with electrodes which have been metallized directly on the crystal body.

For the purpose of examining the sensitivity of different substrate materials when detecting the anaesthetic gas halothane a series of tests with various substrate materials mounted on the detector crystal were carried out with the use of an apparatus according to FIG. 2. In all cases the gaseous mixture investigated was purified laboratory air containing 2% halothane. The crystals used were quartz crystals with a fundamental frequency of 8 MHz and BT-cut and the substrate layer on the detector crystal has, in all instances, a thickness which gave a frequency drop of about 1 kHz for the substrate layer alone. This corresponded to a substrate layer thickness of about 1000 Å when only one side of the detector crystal was coated with the substrate material. The results obtained are shown in Table 1 below, where a minus sign in front of the value of the frequency drop $\Delta f$ shows that the frequency of the detector crystal dropped relative to the frequency of the reference crystal, while a plus sign shows that the frequency of the reference crystal was lower than the frequency of the detector crystal.

TABLE 1

| Substrate | $\Delta f$ Hz |
|---|---|
| Lipid 1, tripalmitin | 0 |
| Lipid 2, egg lecithin | −20 |
| Lipid 3, parafin | +3 |
| Lipid 4, exciccator grease | −8 |
| Silicone oil 1 silicone glycol copolymer Dow Corning DC 190 | −113 |
| Silicone oil 2 polymethylhydrosiloxane Dow Corning DC 1107 | −20 |
| Silicone oil 3 thermosettable polysiloxane dissolved in solvent Dow Corning DC 20 | −12 |
| Silicone oil 4 Silicone glycol copolymer Dow Corning DC 197 | −97 |
| Silicone oil 5 phenylmethylsiloxane Dow Corning DC 702 | +5 |
| Nothing | +4 |

All of the silicone oils used were products produced by Dow Corning Corporation and identified with the product designations given in the table.

As will be seen from the table, the silicone oils 1 and 4, both of which were of the aforementioned kind with large branch chains, exhibit a much higher degree of sensitivity than the remaining silicone oils lacking such large branch chains. The sensitivity to halothane of the various other substances tested was also very slight or generally non-existent. The frequency change observed during the test with both crystals uncoated is thought to be caused by insufficient cleaning of the surface of the crystals.

For the purpose of determining the selectivity of the most sensitive silicone oils according to Table 1 with respect to anaesthetic gases as compared with other gases which might be present when detecting anaesthetic gases and for which other gases the gas detector should not be sensitive, tests were carried out with silicone oil 1 (DC 190) as the substrate material. In this case there were used quartz crystals having a fundamental frequency of 10 MHz and AT-cut, which are somewhat more suitable than the crystals used in the tests according to Table 1. The concentration of the gas component to be detected was 1% in laboratory air where not otherwise stated in the following Table 2, which illustrates the results obtained from the tests.

TABLE 2

| Substance | $\Delta f$ Hz |
| --- | --- |
| Halothane | −150 |
| Enfluorane | −146 |
| Trichloroethylene | −83 |
| Carbon tetrachloride | −55 |
| Alcohol | −27 |
| Toluen | −27 |
| Acetone | −11 |
| Nitrose oxide, N$_2$O, 100% | 0 |
| Water vapor | +9 |
| CO$_2$ 100% | 0 |
| N$_2$ 100% | 0 |
| O$_2$ 100% | 0 |

As will be seen from this table, silicone oil 1 (DV 190) exhibits a very high degree of selectivity with respect to halogenated hydrocarbons, and in particular to the anaesthetic gases halothane and enfluorane, while the sensitivity with respect to other hydrocarbons such as alcohol, toluen and aceton, was relatively slight.

The substrate material according to the invention exhibited no noticeable adsorption of nitros oxide, water vapor, air, oxygen gas, nitrogen gas and carbon dioxide. Corresponding tests were also carried out in respect of the two anaesthetic gases metoxyfluorane and isofluorane which are also halogenated hydrocarbons and for which the substrate material silicone oil 1 (silicone glycol copolymer DC 190) also exhibited a high degree of sensitivity.

Figure 3:
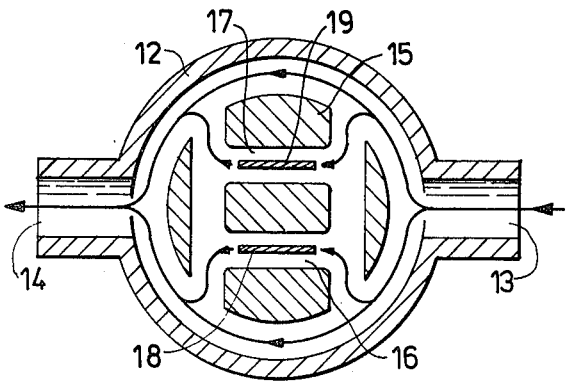
FIG. 3 is a diagram illustrating a typical adsorption-desorption process for an apparatus according to the invention when detecting halothane, alcohol or toluen respectively.
Figure 3:
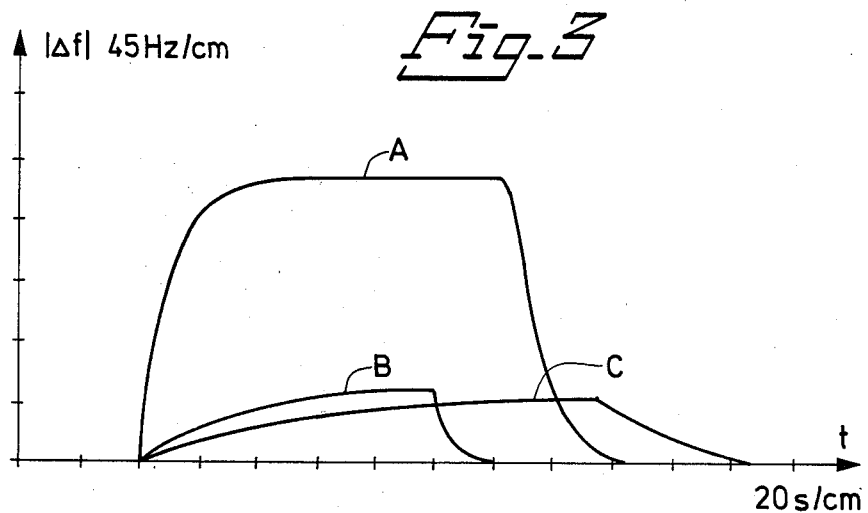

Further tests were carried out for the purpose of studying the adsorption and desorption processes with a substrate layer comprising silicone oil 1 (silicone glycol copolymer DC 190) in respect with firstly the anaesthetic gas halothane and secondly alcohol and toluen which are hydrocarbons for which the sensitivity of the substrate material is low, as shown in Table 2. In all instances the tests were carried out with a concentration of the substance to be detected of 2% in laboratory air and with a substrate layer thickness which gave a frequency lowering of 2.1 kHz for the substrate layer alone. When carrying out the tests purified laboratory air was first caused to flow through the apparatus and, at a given point of time, was replaced with air containing 2% of the substance to be detected. Subsequent to obtaining a steady-state condition in respect of the change in frequency, purified laboratory air was again passed through the apparatus. The adsorption-desorption processes obtained in the tests are illustrated in the diagram illustrated in FIG. 3, in which the curve A represents halothane, the curve B represents alcohol and the curve C represents toluen. As will be seen from FIG. 3, the sensitivity in respect of halothane is much higher than in respect of alcohol and toluen, as already established by the results illustrated in Table 2. It will be seen from the diagram shown in FIG. 3, however, that the reaction rate of the substrate layer is also much greater in respect of halothane than in respect of alcohol and toluen, i.e. the rate of adsorption and desorption is higher. In reality, the fundamental reaction rate of the substrate layer in respect of halothane is much greater than that shown in the diagram of FIG. 3. Thus, the rate at which the halothane molecules was adsorbed and desorbed in the substrate layer when carrying out the tests was primarily determined by the flow conditions of the gas in the connecting lines to the crystal detector and within said detector rather than by the fundamental adsorption and desorption rate of the substrate layer. Tests have been carried out in which attempts were made to supply air containing 0.5% halothane to the whole of the substrated surface of the detector crystal substantially instantaneously. In these tests the substrate comprised silicone oil 1 (DC 190) and had a layer thickness of about 1000 Å. There was obtained a frequency change of 40–50 Hz (steady-state-condition) within the space of about 150 ms. This can be considered a measurement of the fundamental reaction rate of the substrate layer, which has thus been shown to be so high that any variations in dependence on layer thickness lack all practical significance.

Similar comparative adsorption-desorption tests have also been carried out with the use of firstly silicone oil 1 (Silicone glycol polymer DC 190) and secondly a simple silicone oil consisting of polydimethylsiloxane (Dow Corning DC 200) for adsorbing halothane. Similarly large frequency drops in respect of the crystals were obtained with both substrate layers, and hence it can be assumed that the layers had substantially the same thickness. The results obtained in the tests are illustrated in the diagram shown in FIG. 4, in which the curve D represents silicone oil 1 (DC 190), while the curve E represents polydimethylsiloxane. The diagram shows that the silicone oil 1 (Silicone glycol copolymer DC 190) substrate was much more sensitive than the polydimethylsiloxane substrate, which confirms the results shown in Table 1. Further, the diagram of FIG. 4 shows that the silicon oil 1 substrate apparently reacts much more quickly both in respect of adsorption and desorption than the polydimethylsiloxane substrate.

Tests have also been carried out, which show that the frequency drop when using a substrate comprising silicone oil 1 (DC 190), i.e. a silicone oil according to the invention, when detecting the anaesthetic gas halothane in air is linearly proportional to the halothane concentration.

Tests have also been carried out for detecting halothane, in which silicone oil 1 (DC 190) substrate layers, i.e. a silicone oil according to the invention, of differing thickness were used. On this occasion the thinnest substrate layer alone gave a frequency drop of 240 Hz, while the thickest substrate layer alone gave a frequency drop of 4000 Hz. In all instances the concentration of halothane in the laboratory air used as a carrier gas was 2%, and it was found that the lowering in frequency, i.e. the sensitivity of the measuring apparatus, caused by the adsorption of halothane by the substrate layer increased with an increasing layer thickness, whereat the ratio between frequency drop and layer thickness was substantially linear for layer thicknesses above a thickness which resulted in a frequency drop of about 700 Hz for the layer alone.

By way of summary it can be said that when detecting the presence of halogenated hydrocarbons, and in particular the presence of anaesthetic gases such as halothane, enfluorane, metoxyfluorane and isofluorane, substrates comprising silicone oils exhibiting large branch chains or pendant blocks, and in particular silicone glycol copolymers of the type described hereinbefore, have far superior properties with regard to firstly sensitivity but also with regard to reaction rate and selectivity compared with other silicone oils which do not have such large branch chains or pendant blocks.

Although it has been found highly advantageous to measure the variations in the mass of the substrate layer caused by the adsorption and desorption of the gas component to be detected by measuring the variations in the vibrationed frequency of a piezoelectric crystal provided with the substrate layer, there are also other physical properties of the substrate layer affected by the adsorption of the molecules of the gas component to be detected and which can be used for measuring the adsorption of the substrate layer and therewith the concentration of the gas component in question.

Thus, the substrate layer can be applied to a surface with known optical properties and by measuring, for example with the aid of an ellipsometer, the changes in the refraction index of the substrate layer caused by adsorption of the gas component in question on said substrate layer.

The change in the mass of the substrate layer caused by the adsorption of the gas component in question can also be determined by measuring the propagation properties of acoustic surface waves in the layer. For this purpose the substrate layer is suitably applied to a surface of an elongate quartz crystal provided at one end thereof with an electrode structure connected to an acoustic transmitter, for introducing acoustic surface waves in the substrate layer, while the other end of the crystal is provided with a corresponding electrode structure connected to an acoustic receiver.

The electrical impedance of the substrate layer is also changed by adsorption of the detected gas component thereon and can thus be used for measuring purposes. In this case, the substrate layer may be applied to a surface of an electrically insulated carrier body provided with two, finger-shaped electrode structures which mesh with one another and which are embedded in the substrate layer and between which the electrical direct current impedance or alternating current impedance is measured.

What is claimed is:

1. An apparatus for detecting the presence of anaesthetic gases selected from the group consisting of halothane, enfluorance, metoxyfluorane and isofluorane in a mixture of gases, comprising a thin layer of a substrate coated on the surface of a carrier body in such manner that the gas mixture can be brought into contact with the substrate layer, and means for measuring a physical property of said substrate layer which is affected by the amount of gaseous components being adsorbed by the substrate layer, said substrate layer comprising a silicone glycol copolymer.

2. An apparatus as claimed in claim 1, wherein said silicone glycol copolymer has the general structural formula

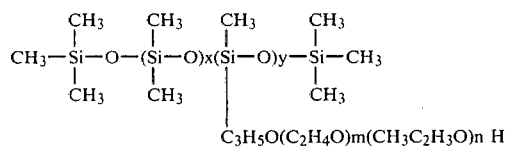

3. An apparatus as claimed in claim 1, wherein said silicone glycol polymer is a random rake copolymer of a trimethylsilylterminated polydimethylsiloxane with pendant silicone-carbon linked blocks of acetate-capped poly-(propylene oxide-ethylene oxide).

4. An apparatus as claimed in claim 1, wherein said silicone glycol polymer is a random rake copolymer of a trimethylsilylterminated polydimethylsiloxane with pendant silicone-carbon linked blocks of hydroxy-terminated poly-(ethylene oxide).

5. An apparatus as claimed in claim 1, wherein said carrier body is a piezoelectric crystal and said measuring means include an oscillator circuit connected to said crystal and means for measuring changes in the oscillating frequency of said oscillator circuit.

6. An apparatus as claimed in claim 5, wherein said measuring means include a second, identical piezoelectrical crystal without any substrate layer, said second crystal being connected to a second, identical oscillator circuit, and circuit means for detecting the frequency difference between the oscillating frequencies of said first and second oscillator circuits.

7. An apparatus as claimed in claim 6, wherein said two crystals are mounted in a common housing designed for permitting a flow of the gas mixture to be analyzed to pass therethrough and in which housing said two crystals are mounted with their side surfaces parallel to the direction of flow of the gas mixture and mutually symmetrically on opposite sides of a symmetry plane through said gas flow.

* * * * *